United States Patent
Zolhayat

(10) Patent No.: US 9,463,077 B2
(45) Date of Patent: Oct. 11, 2016

(54) DENTAL SCALER

(75) Inventor: Hossein Zolhayat, Vancouver (CA)

(73) Assignee: DENTSPLY International Inc., York, PA (US)

(*) Notice: Subject to any disclaimer, the term of this patent is extended or adjusted under 35 U.S.C. 154(b) by 0 days.

(21) Appl. No.: 12/905,830

(22) Filed: Oct. 15, 2010

(65) Prior Publication Data

US 2011/0091837 A1    Apr. 21, 2011

Related U.S. Application Data

(60) Provisional application No. 61/252,360, filed on Oct. 16, 2009.

(51) Int. Cl.
*A61C 1/07* (2006.01)
*A61C 1/00* (2006.01)
*A61C 17/20* (2006.01)

(52) U.S. Cl.
CPC .............. *A61C 1/07* (2013.01); *A61C 1/0015* (2013.01); *A61C 1/0061* (2013.01); *A61C 17/20* (2013.01)

(58) Field of Classification Search
CPC ............... A61C 1/0007–1/0023; A61C 17/20
USPC ................... 433/143, 118–119, 80, 86, 216; 601/162; 606/169
See application file for complete search history.

(56) References Cited

U.S. PATENT DOCUMENTS

| | | | |
|---|---|---|---|
| 3,526,036 A | | 9/1970 | Goof |
| 3,983,344 A | * | 9/1976 | Straihammer ............... 200/86.5 |
| 4,820,152 A | * | 4/1989 | Warrin et al. ................... 433/86 |
| 5,754,016 A | | 5/1998 | Jovanovic et al. |
| 6,190,167 B1 | * | 2/2001 | Sharp ........................... 433/119 |
| 7,133,717 B2 | * | 11/2006 | Coston et al. ................... 604/20 |
| 7,435,085 B2 | | 10/2008 | Gugel et al. |
| 7,488,173 B2 | | 2/2009 | Bochi |
| 2005/0261715 A1 | * | 11/2005 | Boukhny et al. ............. 606/169 |
| 2006/0020310 A1 | * | 1/2006 | Loebel et al. ................... 607/89 |
| 2006/0063127 A1 | * | 3/2006 | Gugel et al. .................... 433/82 |
| 2006/0188841 A1 | * | 8/2006 | Edel et al. ..................... 433/119 |
| 2006/0269900 A1 | * | 11/2006 | Paschke et al. .............. 433/119 |
| 2007/0079455 A1 | * | 4/2007 | Brewer et al. ................. 15/22.2 |
| 2008/0193893 A1 | * | 8/2008 | Beck ............................... 433/27 |

OTHER PUBLICATIONS

The SSC Controls Company. "Light Duty Foot Switches". Jul. 3, 2008. Accessed via Internet Archive Wayback Machine at http://www.ssccontrols.com/homepage-lightduty.htm.*
http://www.lysta.dk/ultrasonic-scalers/hygienist-2420-1—published Dec. 11, 2008.

* cited by examiner

*Primary Examiner* — Edward Moran
(74) *Attorney, Agent, or Firm* — Leana Levin; Douglas J. Hura; David A. Zdurne

(57) ABSTRACT

An ultrasonic dental scaler includes a handpiece and a control unit. The handpiece has a tip, and a water irrigator for providing water to the tip, the handpiece being constructed and arranged to vibrate the tip. The control unit is in communication with the handpiece and receives electrical feedback from the tip. The control unit automatically controls water flow from the water irrigator to the tip and the vibration of the tip based on the received electrical feedback.

10 Claims, 5 Drawing Sheets

DENTAL SCALER

CROSS REFERENCE TO RELATED APPLICATIONS

This application claims the benefit of Provisional Application No. 61/252,360, filed on Oct. 16, 2009, the entire contents of which is incorporated herein by reference.

FIELD OF TECHNOLOGY

The present disclosure relates to dental scalers including, but not limited to, ultrasonic dental scalers with power and irrigation control.

BACKGROUND

Dental scalers are used to remove plaque buildup and calculus for from teeth. Traditionally, dentists had used simple scaler instruments to manually remove plaque and calculus from a patient's teeth. More recently, ultrasonic dental scalers, which utilize a tip that vibrates at high speeds, have been developed. The ultrasonic dental scaler tip is applied to a tooth and the vibration causes the plaque and calculus buildup to be removed from the tooth.

Improvements in dental scalers are desirable.

SUMMARY

According to one aspect an ultrasonic dental scaler comprises a handpiece and a control unit. The handpiece includes a tip and a water irrigator for providing water to the tip. The handpiece is arranged and constructed to vibrate the tip. The control unit is in communication with the handpiece to receive electrical feedback from the tip and automatically control water flow from the water irrigator to the tip and the vibration of the tip based on the received electrical feedback In some embodiments, the handpiece comprises a coil for vibrating the tip; and the control unit comprises a sensor coupled to the coil for sensing a variable signal of the coil.

In various embodiments, the control unit further comprises: a coil driving circuit for providing power to the coil; and a control circuit to: receive data from the sensor; and adjust the power provided to the coil and the water provided to the tip based on the data received.

In some embodiments, the dental scaler further comprises: a plurality of solenoids in fluid communication with the irrigator. Each solenoid has an energized position for providing water to the irrigator and an off position. The control circuit controls water flow by energizing and turning off one of the plurality of solenoids.

According to another aspect, a circuit board for use with an ultrasonic dental scaler, the dental scaler having a handpiece that includes a tip and an irrigator, the circuit board comprises: a sensor for coupling to the tip to receive electrical feedback form the tip; and a control circuit coupled to the sensor to automatically adjust power and an amount of water provided to the tip based on the electrical feedback received.

In some embodiments, the handpiece comprises a coil for vibrating the tip; and the circuit board further comprises a sensor for coupling to the coil to sense a variable signal of the coil.

In various embodiments, the circuit board further comprises: an irrigation control circuit to: receive data from the sensor; and adjust the water provided to the tip based on the data received; and a central circuit to: receive data from the sensor; and adjust the power provided to the tip based on the data received.

In some embodiments the scaler further comprises a plurality of solenoids in fluid communication with the irrigator. Each solenoid has an energized position for providing water to the irrigator and an off position. The irrigation control circuit controls water flow by energizing and turning off one of the plurality of solenoids.

In some embodiments, the circuit board comprises a foot control circuit for controlling a foot control of the ultrasonic dental scaler.

According to another aspect, a method of operating a dental scaler having a tip comprises: applying the tip of the dental scaler to a tooth; providing power and water to the tip; receiving electrical feedback from the tip; and adjusting the amount of power and water provided to the tip based on the feedback received.

In some embodiments, the power is provided to the tip through a coil; and receiving electrical feedback from the tip comprises sensing a signal on the coil.

Other aspects and features of the present disclosure will become apparent to those ordinarily skilled in the art upon review of the following description of example embodiments in conjunction with the accompanying figures.

BRIEF DESCRIPTION OF THE DRAWINGS

Embodiments of the present disclosure will now be described, by way of example only, with reference to the accompanying figures.

DETAILED DESCRIPTION

Figure 1:
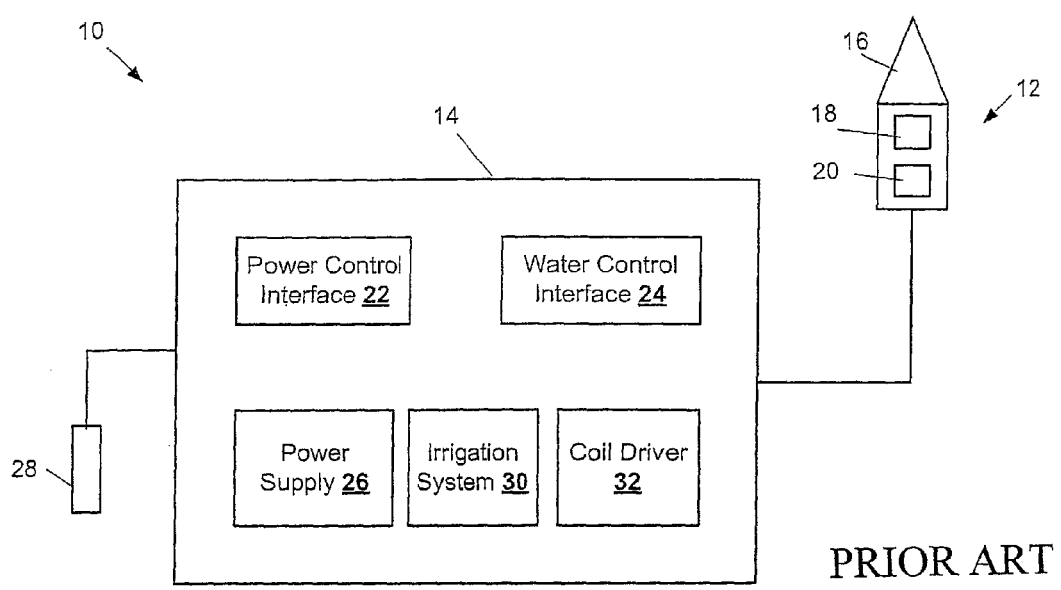
FIG. 1 is a block diagram of a known ultrasonic dental scaler.

The following describes an ultrasonic dental scaler that includes a handpiece and a control unit. The handpiece includes a tip and a water irrigator for providing water to the tip. The handpiece is constructed and arranged to vibrate the tip. The control unit is in communication with the handpiece and receives electrical feedback from the tip. The control unit is configured to automatically control water flow from the water irrigator to the tip and the vibration of the tip based on the received electrical feedback.

For simplicity and clarity of illustration, reference numerals may be repeated among the figures to indicate corresponding or analogous elements. Numerous details are set forth to provide an understanding of the embodiments described herein. The example embodiments may be practiced without these details. In other instances, well-known methods, procedures, and components have not been described in detail to avoid obscuring the embodiments described. The description is not to be considered as limited to the scope of the example embodiments described herein.

Prior to the advent of ultrasonic dental scalers, dentists and other oral healthcare professionals utilized simple scaler instruments to remove plaque and calculus from the patient's teeth.

Proper and efficient use of these instruments depended on the operator's skills. For example, if insufficient pressure was applied to the calculus buildup, the instrument would not remove the buildup and the treatment would have to be repeated. Similarly, if too much pressure was applied, the treatment may damage the tooth enamel.

Reference is now made to FIG. 1, which is a block diagram of a known ultrasonic dental scaler 10. Dental scaler 10 includes a handpiece 12 and a control unit 14. The handpiece comprises a tip 16, a handpiece coil 18, and an irrigator 20.

Control unit 14 includes a power control interface 22 and water control interface 24. Power control interface 22 generally comprises a knob. Water control interface 24 also generally comprises a knob. Control unit 14 also includes a power supply 26, a foot control 28 and irrigation system 30. The power supply supplies power to each of the electronic components of scaler 10.

Control unit 14 also includes a coil driver circuit 32 that is coupled to coil 18 of handpiece 12. Coil driver circuit 32 provides a signal, such as for example a sine wave, having a suitable frequency to handpiece coil 18. This activates handpiece coil 18 and that in turn causes tip 16 to vibrate.

When operating scaler 10, an operator is able to remove plaque and calculus from a tooth by touching tip 16 to the plaque and calculus on the tooth surface. In order to remove hard calculus, the operator can increase the power by adjusting the power knob of power interface 22 on the control unit, which in turn adjusts the amplitude of the signal provided to the tip.

The high frequency vibrations of the tip cause the tip to heat up. The operator is able to cool the tip by controlling the water flow provided by irrigator 20 to tip 16 through the use of water control interface 22. As the heat increases on the ultrasonic dental scaler tip 16, the operator may increase the water flow to the tip 16 and as the heat decreases, the operator may decrease the water flow to tip 16.

In known systems, when using a dental scaler 10, the operator adjusts the power and water levels through power control interface 22 and water control interface 24. The operator then applies the tip to an operator's teeth and uses foot control 28 to cause scaler 10 to begin operation.

Two types of handpieces are commonly used in known scaler systems. The first is a piezoelectric based design and the second is an electromagnetic based design. In the piezoelectric handpieces, the unit's output frequency is applied to a series of crystal stacks and according to the characteristics of crystals, the electrical energy is converted to mechanical energy which in turn is transmitted to the tip as a mechanical movement. In the electromagnetic handpiece, the unit's output frequency is applied to the handpiece coil and then to the end part of the tip which is made of iron stacks that act as the handpiece iron core which then converts the electrical energy into the mechanical energy which vibrates the handpiece tip. Handpeice 12 of dental scaler 10 can be any suitable handpiece including, but not limited to, a piezoelectric handpiece and an electromagnetic handpiece.

When scaler 10 is turned on by an operator, scaler 10 is generally in a standby mode and as the operator pushes on a foot pedal of foot control 28, the handpiece is activated and the treatment can be started. Appropriate settings for the water and power can be learned by an operator through skill and experience. The power and water knobs of power control interface 22 and water control interface 24 are adjusted by the operator.

A problem of known scalers is that, if the operator would like to change the amount of power and/or water supplied to the tip, the operator must stop the treatment and then adjust the knobs. If insufficient water is supplied to tip 16, then tip 16 may become overheated and the patient may experience pain. If insufficient power is supplied to tip 16, plaque and calculus is not removed as easily and the scaling time increases. In general known systems do not have default settings that can help an operator choose appropriate manual settings. This lack of default settings as well as the need to stop the treatment in order to adjust power and water flow settings can make a scaler difficult to use especially for inexperienced operators.

Figure 2:
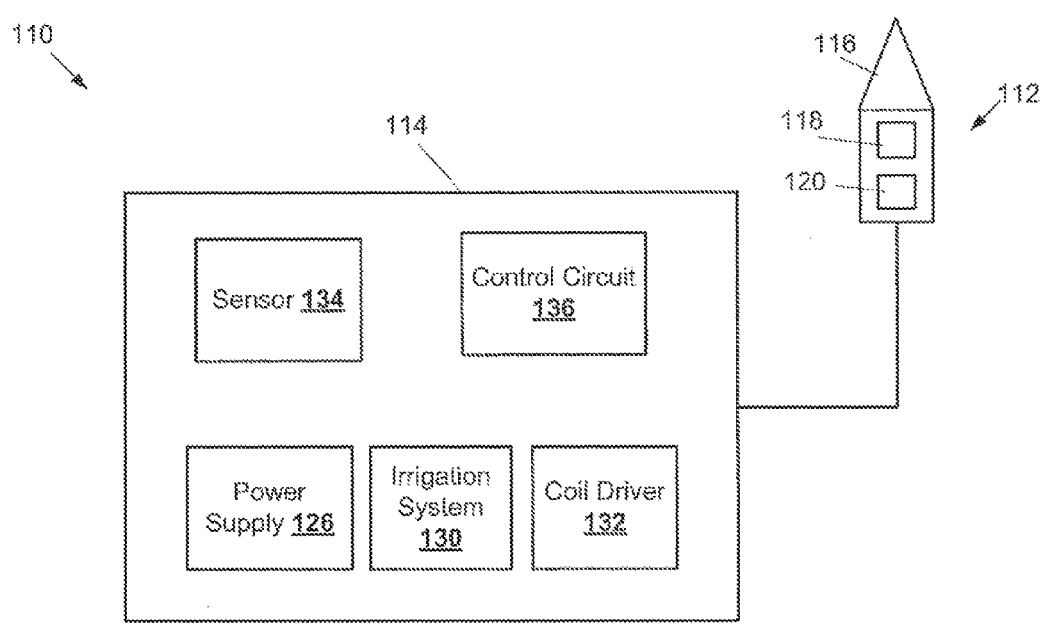
FIG. 2 is a block diagram of an ultrasonic dental scaler, according to various embodiments.

Reference is now made to FIG. 2, which is a block diagram of a dental scaler 110 according to various embodiments. Scaler 110 comprises a handpiece 112 and a control unit 114. The handpiece 112 comprises a tip 116, a handpiece coil 118, and an irrigator 120 for providing water to tip 116. Handpeice 112 of dental scaler 110 can be any suitable handpiece including, but not limited to, a piezoelectric handpiece and an electromagnetic handpiece.

Control unit 114 includes a power supply 126, an irrigation system 130, a coil driver circuit 132, a sensor circuit 134, and a control circuit 136. The power supply supplies power to each of the electronic components of scaler 110.

Coil driver circuit 132 is coupled to handpiece 112 and provides a suitable signal, such as for example a sine wave, having a suitable frequency to handpiece coil 118. This activates handpiece coil 118 and that in turn causes tip 116 to vibrate.

Sensor 134 is coupled to handpiece 112 and receives feedback from tip 116 regarding the loading of tip 116. In some embodiments, sensor 134 is an electronic circuit that is coupled to handpiece coil 118 and detects the signal present on the handpiece coil 118. In some embodiments, sensor 118 samples the signal on handpiece coil 18. In some embodiments, sensor 134 senses the small loading variation encountered by coil 18 based on the principle of magnetostrictics. The amplitude of the signal, which for example can be a sine wave voltage, varies based on the friction that tip 116 encounters. The load at tip 116 is dependent on the friction encountered by tip 116 which in turn is dependent upon the force applied by the operator. The applied force may be adjusted based on characteristics of the surface of the tooth, such as for example, the hardness and the amount of plaque and calculus buildup on the tooth surface. The amplitude of the signal sensed by sensor 134 is indicative of the friction and loading encountered by tip 116. Higher amplitude samples correspond to greater friction and a greater load. This principle is similar to a running electromotor that turns a shaft. If the shaft encounters a great load, a counter electromotive force is produced that requires a greater current to react to the load change. In other words, as the load increases a greater amount of current passes through the motor coil. A similar result occurs in the handpiece coil.

Electronic sensor 134 processes the samples received from the handpiece coil 118 and provides data to other components such as control circuit 136. In some embodiments, the data provided by electronic sensor 134 to other components of scaler 110 comprises a reference voltage.

In some embodiments, irrigation system 130 comprises a series of water regulator solenoids. In other embodiments, irrigation system 130 comprises a stepper motor that turns a water regulator shaft in order to regulate water flow to tip 116.

Control circuit 136 is coupled to sensor 134 and receives data regarding the loading of tip 116. Based on the loading of tip 116, control circuit 136 controls the power applied to tip 116 by circuit 132. Control circuit 136 also controls irrigation system 130 based on, for example, the power supplied to coil 118 and/or the loading of tip 116. Accordingly control circuit 136 controls both the power and the water that is supplied to tip 116.

It should be understood that the functionality of any particular circuit or component of scaler 110 need not be confined to a single circuit. For example, although control circuit 136 is described and illustrated as a single circuit it should be understood that in some embodiments, the logic circuits that make up control circuit 136 can be distributed throughout scaler 110. For example, the irrigation control functionality of control circuit 136 in some embodiments comprises part of irrigation system 130 while the coil driver 132 can comprise logic for controlling the amount of power supplied to coil 118.

In various embodiments, scaler 110 automatically adjusts the scaling power and water settings based on the load at tip 116 which may be varied based on characteristics, such as hardness of the plaque or calculus buildup present on a patient's tooth. The power setting is adjusted by control circuit 136 based on variable electrical feedback received by sensor 134 from tip 116. Control circuit 136 also adjusts the water setting based on the power supplied to tip 116 or the variable electrical feedback received by sensor 134 from tip 116. Accordingly, the operator is not required to set or adjust the scaler power or water settings while operating scaler 110. Accordingly, unlike with known scalers, an operator need not stop operation of the scaler 110 when switching from one tooth surface to another with differing plaque or calculus characteristics.

Some embodiments described herein relate to a controller board that is utilized to modify a known ultrasonic scaler such as, for example, scaler 10. The circuit board is configured to control the power and water flow settings of scaler 10 such that scaler 10 operates in a manner that is substantially similar to scaler 110 as described above.

Figure 3:
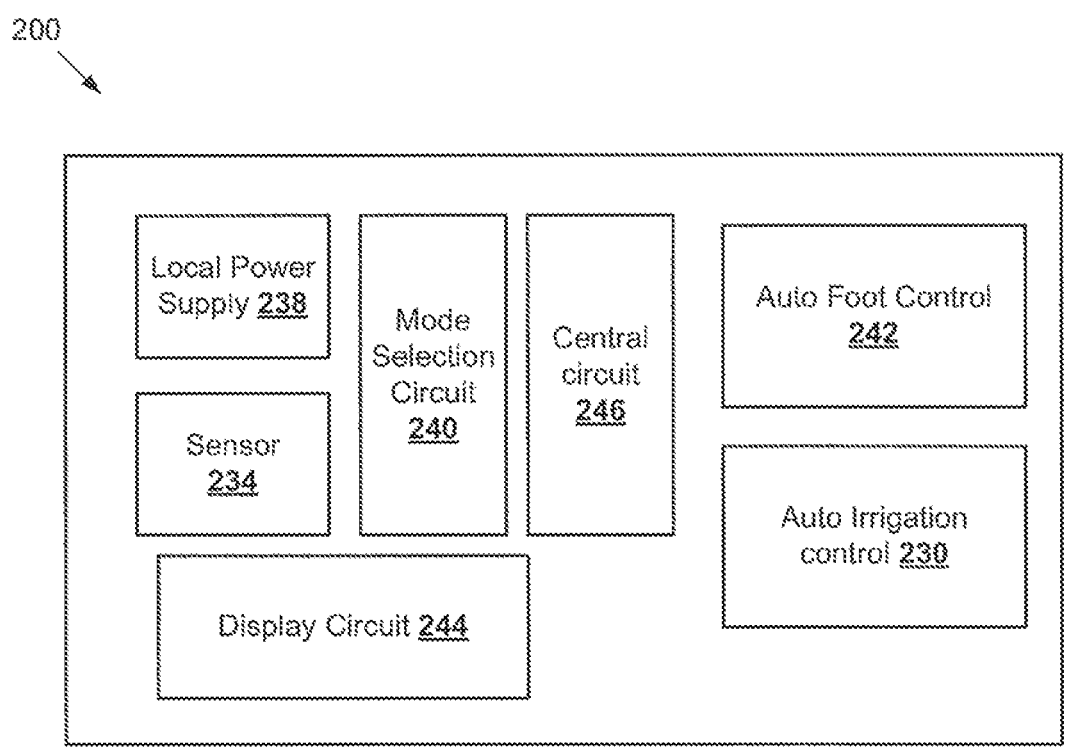
FIG. 3 is a block diagram of a circuit board for use with a known ultrasonic dental scaler, according to various embodiments.

Reference is now made to FIG. 3, which is a block diagram of a circuit board 200 for use with a known scaler system such as, for example, scaler 10. Circuit board 200 comprises an auto irrigation circuit 230, a sensor 234, a central circuit 246, a local power supply 238, a mode selection circuit 240, and an automatic foot control circuit 242.

Local power supply 238 provides power to the components of circuit board 200. Known scalers 10 generally provide an unregulated 24 V supply. In some embodiments, local power 238 provides one or more regulated voltages that are utilized by the various components of circuit board 200. For example, in some embodiments, local power supply 238 serves as both a regulated 5 V power supply and a regulated 15 V power supply.

Sensor 234 is coupled to handpiece 12 and receives feedback from tip 16 regarding the loading of tip 16. In some embodiments, sensor 234 comprises an electronic circuit that is coupled to handpiece coil 18 and senses the voltage variations on the handpiece coil 18. Sensor 234 processes the received signals and provides data to various components of the circuit board 200. In some embodiments, the data provided to other components by sensor 234 comprises a reference voltage. The operation of sensor 234 is similar to sensor 134 described above. In various embodiments, the input connections of sensor 134 are connected in parallel with the coil driver 32 output connections or the input connections of coil 18.

Mode selection circuit 240 allows the operator to select a mode of operation. Mode selection circuit 240 comprises any appropriate operator interface, such as, for example, but not limited to, a switch, a knob, or a keypad to allow selection of a mode. In some embodiments, there are two modes of operation. In the first mode, circuit board 200 controls various components of the dental scaler to cause the dental scaler to operate in a manner similar to scaler 110. In the second mode, circuit board 200 is not active and allows the scaler 10 to be operated as if circuit board 200 were not present.

Central circuit 246 interconnects various components of circuit board 200 and various components of dental scaler 10. For example, central circuit 246 receives a reference voltage from sensor 234 and according to the reference voltage adjusts the amount of power supplied to coil 18 by coil driver 32.

In some embodiments, the foot control circuit 242 is connected in parallel with the foot pedal of foot control 28. When circuit board 200 is in the first mode, foot control circuit 242 controls foot control 28 and allows the operator to operate scaler 10 without pressing on the foot control. Foot control circuit 242 includes a driver circuit for driving the foot control circuitry.

In some embodiments, after the first mode is selected by the operator, foot control circuit 242 provides a delay before allowing scaler 110 to begin operation. In some embodiments, the delay is provided by a one-shot trigger monostable. The delay can be selected to, for example, ensure that that the scaler is not operated in the first mode until the entire circuit board 200 is ready to operate.

In some embodiments, foot control circuit 242 also includes a retriggerable monostable. This second monostable is used to provide a time delay for switching circuit board 200 out of the first mode and causes scaler 10 to go into a sleep mode. In some embodiments, the delay is 30 seconds. In some embodiments, each time the operator touches a tooth with tip 16, the monostable is retriggered. If however, the monostable is not retriggered for a time period equal to the delay, then the circuit board 200 causes scaler 10 to go into a sleep mode. In some embodiments, a single push to the foot pedal of foot control 28 cases scaler 10 to exit the sleep mode.

In some embodiments that contain both the one shot trigger monostable and the re-trigerrable monostable, the foot control circuit 242 does not drive the foot control circuitry until after both monostables have been activated.

Automatic irrigation circuit 230 receives data from sensor 234. The data received from irrigation circuit 230 comprises any suitable data, including but not limited to, data indicative of the power supplied to coil tip 18 and/or the loading on tip 16. In some embodiments, automatic irrigation circuit 230 includes control logic for determining an amount of water to be supplied to tip 16 based on the data received. Automatic irrigation circuit 230 adjusts the amount of water provided by irrigation system 30 to tip 16 based on the data received. For example, in some embodiments, automatic irrigation circuit 230 includes water flow valve driver circuits that control the water valves of irrigation system 30. In various embodiments, automatic irrigation circuit 230 also includes a circuit for supplying power to irrigator 20 of handpiece 12.

In some embodiments, when circuit board 220 is installed in a known ultrasonic scaler 10, circuit board 220 does not generally alter the performance of the scaler 10 in the sense that various components of scaler 10 continue to function as intended and designed by the manufacturer. In other words, in some embodiments, scaler 10 continues to operate as designed by the manufacturer except that the operator can operate scaler 10 without selecting or adjusting power and water settings.

In some embodiments, circuit board 200 can be utilized as an add on feature for known scalers such as scaler 10. Circuit board 200 can be installed in scaler 10 and other than the connections made to circuit board 200 modifications to the original circuitry scaler 10 including the handpiece 12 and control unit 14 may not be made. In addition, through the use of the mode selection feature, if desired, circuit board 200 can be disabled at any time and then scaler 10 functions in the same manner as if circuit board 200 were not installed. In some embodiments, circuit board 200 does not utilize large amounts of power and can feed off the existing power supply of scaler 10 without modifying the existing power supply. In some embodiments, the low power requirements of circuit board 200 can be achieved through the use of CMOS integrated circuits.

In some embodiments, circuit board 200 includes a display circuit 244. Display circuit 244 includes a display which can be for example, a liquid crystal display (LCD) or light emitting diode (LED) display. Display circuit 244 receives data regarding the power provided to coil tip 18. The data can be received from, for example, sensor 234. Based on the data received, display circuit 244 displays and indication of the amount of power being provided to the tip.

In some embodiments, circuit board 200 includes an interface for allowing the operator to limit the power that central circuit 246 causes coil driver 32 to supply to coil 18. For example, the operator may select any suitable power level limit. In some embodiments, the operator can select a particular percentage of the total power to serve as a limit. In some embodiments, the interface comprises a connection to power interface 22 of scaler 10 such that the operator can utilize power interface 22 to select a maximum power level when circuit board 200 is operated in the first mode.

Figure 4:
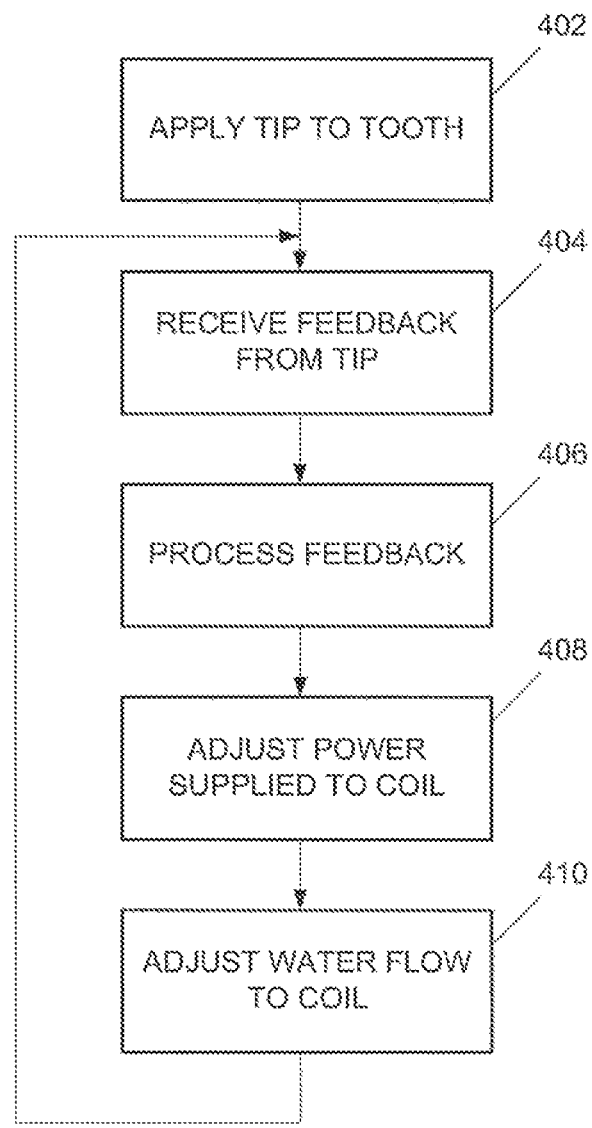
FIG. 4 is a flow chart diagram illustrating the basic operation of the ultrasonic dental scaler of FIG. 2.

Reference is now made to FIG. 4 which illustrates a flow chart diagram of the operation of scaler 110 according to various embodiments. FIG. 4 is also applicable to a scaler 10 with circuit board 200 installed and operating in the first mode.

The scaler tip is applied to a tooth at 402.

Feedback is received from the tip 16 or 116 at 404.

The feedback received from the tip is processed by sensor 134 or 234 at 406.

The power applied to the handpiece coil is adjusted based on the feedback received from tip 16 or 116 at 408.

The water supplied to the handpiece tip 16 or 116 is adjust based the feedback received from the tip 16 or 116 at 410.

Figure 5:
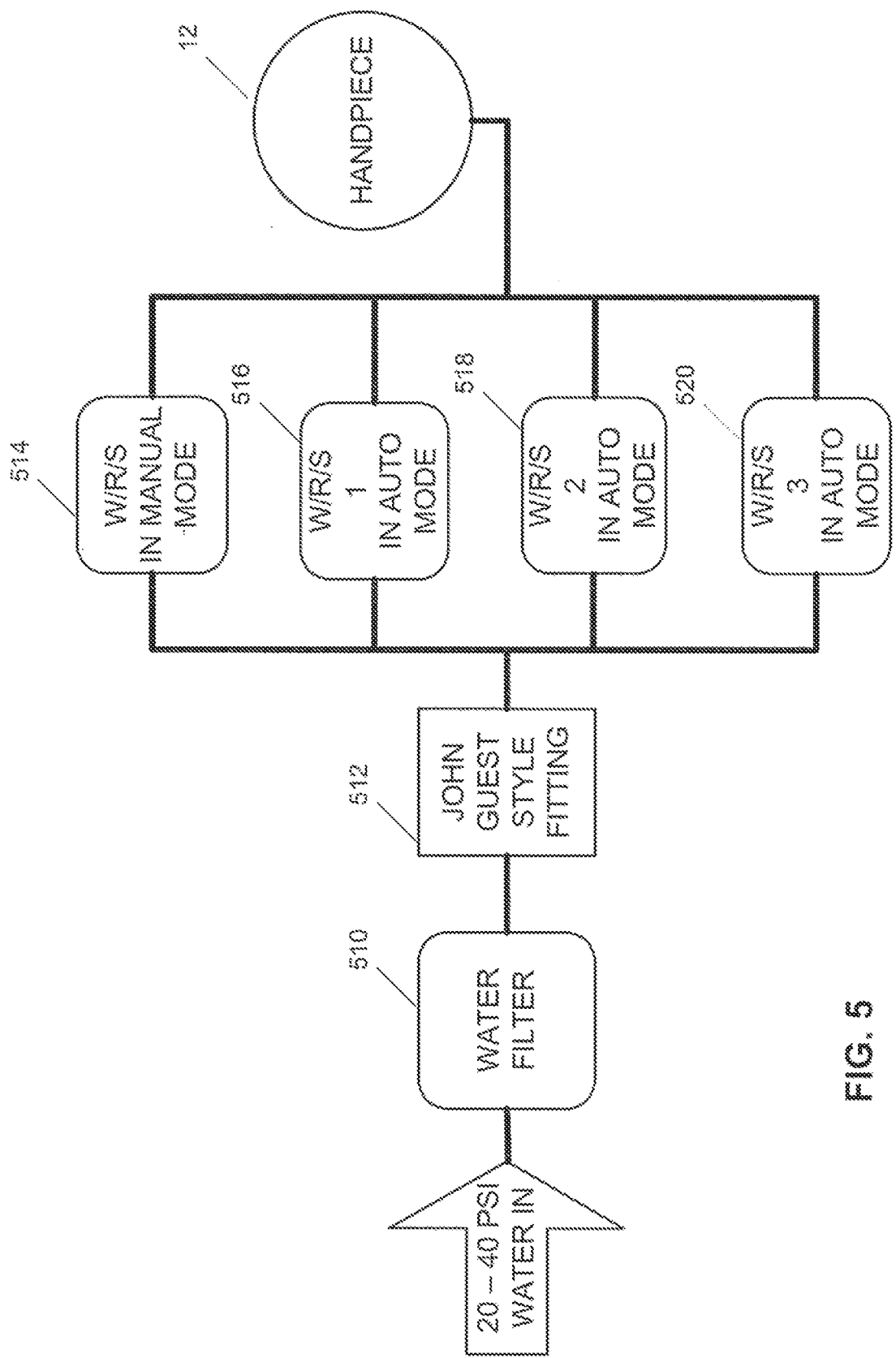
FIG. 5 is a schematic diagram illustrating the flow of water according to an embodiment.

In some embodiments, when circuit board 200 is installed in a scaler 10, the irrigation system 30 may be modified by adding water regulators or solenoids that are controlled by the automatic irrigation control circuit 200. Reference is now made to FIG. 5, which is a schematic diagram illustrating the water flow through irrigation system 130 of scaler 110 or through irrigation system 30 of scaler 10 when circuit board 200 is installed, according to various embodiments. The irrigation system provides water at 20 to 40 PSI. The water enters a filter 510 and then into a John Guest style fitting 510. The water is then fed into water regulators or solenoids 514, 516, 518, and 520. If the operator has selected the second mode of operation through circuit board 200, then solenoid 514 is utilized by adjusting the knob of water control interface 24. If the operator has selected the first mode of operation through circuit board 200, then solenoids 516, 518, and 520 are utilized to adjust water flow.

In some embodiments, each solenoid used in the first mode is either energized or off. Accordingly, each solenoid is operated as fully on or off. In some embodiments, each solenoid provides a given flow of water. Accordingly, if each solenoid provides the same amount of water flow, the arrangement illustrated in FIG. 5 allows for three different levels of water flow. The precision at which water flow can be controlled can be increased by, for example, utilizing a greater number of solenoids.

In some embodiments, of scaler 110 control circuit 136 controls the solenoids by energizing or turning each solenoid off. In some embodiments of circuit board 200, irrigation control circuit 230 controls the solenoids by energizing or turning each solenoid off.

The above-described embodiments are intended to be examples only. Alterations, modifications and variations can be effected to the particular embodiments by those of skill in the art without departing from the scope, which is defined solely by the claims appended hereto.

What is claimed is:

1. An ultrasonic dental scaler comprising:
a handpiece including a tip, and a water irrigator for providing water to the tip, the handpiece arranged and constructed to vibrate the tip;
a control unit in communication with the handpiece to:
receive electrical feedback from the tip; and
automatically adjust water flow from the water irrigator to the tip and the vibration of the tip based on the received electrical feedback, wherein the received electrical feedback correlates to a load on the tip, and
a circuit board comprising an autoirrigation circuit, a sensor, a central circuit, a local power supply, a mode selection circuit, and a foot control circuit,
the foot control circuit being capable of controlling a foot control of the ultrasonic dental scaler, such that the ultrasonic scaler is activated by an operator initially pushing on the foot control, but the ultrasonic scaler is capable of being controlled by an operator without pressing on the foot control and wherein the foot control circuit comprises a one-shot trigger monostable and a retriggerable monostable.

2. The dental scaler of claim 1, wherein the handpiece comprises a coil for vibrating the tip; and
wherein the sensor is coupled to the coil for sensing a variable signal of the coil.

3. The dental scaler of claim 2, further comprising
a coil driving circuit for providing power to the coil; and
the central circuit is capable of:
receiving data from the sensor; and
adjusting the power provided to the coil and the water provided to the tip based on the data received.

4. The dental scaler of claim 3, further comprising:
a plurality of solenoids in fluid communication with the irrigator, each solenoid having an energized position for providing water to the irrigator and an off position; and
wherein the central circuit controls water flow by energizing and turning off one of the plurality of solenoids.

5. A circuit board for use with an ultrasonic dental scaler, the dental scaler having a handpiece that includes a tip and an irrigator, the circuit board comprising:
a local power supply,
an auto irrigation circuit,
a sensor for coupling to the tip to receive electrical feedback from the tip;
a central circuit coupled to the sensor to automatically adjust power and an amount of water provided to the tip based on the electrical feedback received, wherein the received electrical feedback correlates to a load on the tip, and a mode selection circuit, and a foot control circuit for controlling a foot control of the ultrasonic dental scaler, such that the ultrasonic scaler is activated by an operator initially pushing on the foot control, but the ultrasonic scaler is capable of being controlled by an operator without pressing on the foot control and wherein the foot control circuit comprises a one-shot trigger monostable and a retriggerable monostable.

6. The circuit board of claim 5, wherein the handpiece comprises a coil for vibrating the tip; and wherein the circuit board further comprises the sensor for coupling to the coil to sense a variable signal of the coil.

7. The circuit board of claim 6, wherein the auto irrigation circuit is capable of:

receiving data from the sensor; and adjusting the water provided to the tip based on the data received; and wherein the central circuit is capable of:

receiving data from the sensor; and adjusting the power provided to the tip based on the data received.

8. The circuit board of claim 7, wherein the scaler further comprises a plurality of solenoids in fluid communication with the irrigator, each solenoid having an energized position for providing water to the irrigator and an off position; and wherein the auto irrigation circuit controls water flow by energizing and turning off one of the plurality of solenoids.

9. A method of operating a dental scaler having a tip, the method comprising:

applying the tip of the dental scaler to a tooth;

applying pressure on a foot control in a single push to activate the dental scaler such that an operator can continue operating the dental scaler without continually pressing on the foot control, providing power and water to the tip;

receiving electrical feedback from the tip; and adjusting the amount of power and water provided to the tip based on the feedback received, wherein the received feedback correlates to a load on the tip, and changing an operational mode of the dental scaler by triggering a one-shot trigger monostable and a retriggerable monostable in a foot control circuit.

10. The method of claim 9, wherein the power is provided to the tip through a coil; and wherein receiving electrical feedback from the tip comprises sensing a signal on the coil.

\* \* \* \* \*